United States Patent
Johnson

(10) Patent No.: US 10,842,385 B2
(45) Date of Patent: Nov. 24, 2020

(54) VASCULAR IMPEDANCE MEASURING DEVICE AND METHOD OF DETERMINING IMPEDANCE

(71) Applicant: RUSH UNIVERSITY MEDICAL CENTER, Chicago, IL (US)

(72) Inventor: Andrew Kelly Johnson, Chicago, IL (US)

(73) Assignee: Rush University Medical Center, Chicago, IL (US)

( * ) Notice: Subject to any disclaimer, the term of this patent is extended or adjusted under 35 U.S.C. 154(b) by 504 days.

(21) Appl. No.: 15/316,018

(22) PCT Filed: Jun. 1, 2015

(86) PCT No.: PCT/US2015/033566
§ 371 (c)(1),
(2) Date: Dec. 2, 2016

(87) PCT Pub. No.: WO2015/187573
PCT Pub. Date: Dec. 10, 2015

(65) Prior Publication Data
US 2017/0086682 A1    Mar. 30, 2017

Related U.S. Application Data

(60) Provisional application No. 62/007,240, filed on Jun. 3, 2014.

(51) Int. Cl.
*A61B 5/026* (2006.01)
*A61B 5/021* (2006.01)
(Continued)

(52) U.S. Cl.
CPC ........ *A61B 5/02007* (2013.01); *A61B 5/0031* (2013.01); *A61B 5/021* (2013.01);
(Continued)

(58) Field of Classification Search
CPC ... A61B 5/02007; A61B 5/0031; A61B 5/021; A61B 5/0215; A61B 5/026;
(Continued)

(56) References Cited

U.S. PATENT DOCUMENTS

| | | |
|---|---|---|
| 5,873,835 A | 2/1999 | Hastings et al. |
| 7,794,403 B2 | 9/2010 | Schaafsma |
| 8,271,080 B2 | 9/2012 | Thompson et al. |

OTHER PUBLICATIONS

Tyberg et al., "Wave intensity analysis and the development of the reservoir-wave approach," Med. Biol. Eng. Comput., 47:221-232 (2009).

(Continued)

*Primary Examiner* — Navin Natnithithadha
(74) *Attorney, Agent, or Firm* — Barnes & Thornburg LLP; Alice O. Martin

(57) ABSTRACT

A vascular impedance measuring device may comprise a processing component capable of processing raw pressure and flow wave data and a pressure measuring component capable of providing pressure wave data from a specified point in a vessel and forwarding the pressure wave data to the processing component. The device may further include a flow measuring component capable of providing flow wave data from the specified point or a point near the specified point in the vessel and forwarding the flow wave data to the processing component. The processing component processes the raw pressure and flow wave data to produce an estimation of vascular impedance of the vessel from the specified point of measure and may provide data to a feedback system for therapy.

17 Claims, 10 Drawing Sheets

(51) Int. Cl.
*A61B 5/0215* (2006.01)
*A61B 5/02* (2006.01)
*A61B 5/00* (2006.01)

(52) U.S. Cl.
CPC ............ *A61B 5/026* (2013.01); *A61B 5/0215* (2013.01); *A61B 5/486* (2013.01); *A61B 5/4839* (2013.01); *A61B 5/6852* (2013.01); *A61B 5/7278* (2013.01); *A61B 5/7425* (2013.01)

(58) Field of Classification Search
CPC ..... A61B 5/4839; A61B 5/486; A61B 5/6852; A61B 5/7278; A61B 5/7425
USPC .......................... 600/481, 483, 485, 486, 488
See application file for complete search history.

(56) References Cited

OTHER PUBLICATIONS

Search Report and Written Opinion issued in Int'l App. No. PCT/US2015/033566 (dated 2015).

VASCULAR IMPEDANCE MEASURING DEVICE AND METHOD OF DETERMINING IMPEDANCE

CROSS REFERENCE TO RELATED APPLICATIONS

This application is a U.S. nationalization under 35 U.S.C. § 371 of International Application No. PCT/US2015/033566, filed Jun. 1, 2015, which claims the benefit of priority under 35 U.S.C. § 119(e) to U.S. Provisional Application Ser. No. 62/007,240, filed Jun. 3, 2014. The disclosures set forth in the referenced applications are incorporated herein by reference in their entireties.

FIELD OF THE DISCLOSURE

The present disclosure relates generally to medical devices and, more specifically, to medical devices for monitoring vasculature of mammals. The monitoring of vessels can be useful in determining whether particular conditions are present in mammals.

BACKGROUND OF THE DISCLOSURE

The impedance or resistance to flow in mammalian vasculature is increased in diseased states, generally those that restrict blood flow. Two such diseased states include vessel stenosis and vessel vasospasm (constriction). Diagnosis of diseased states is important in guiding treatment of altered blood flow to maintain adequate blood perfusion of organs and to prevent worsening conditions. Methods have been developed to approximate impedance of the entire vasculature, but they do not provide useful information regarding specific vessels. Other methods have been developed to approximate impedance across a vessel segment using measurements, usually blood pressure, proximal and distal to the specified segment.

There is currently no clinically useful method to measure impedance of a single vessel or distal vessel tree using proximal measurements only. Examples of this situation include cerebral artery vasospasm, which occurs after a subarachnoid hemorrhage. Adequate measurement of the arteries distal to the site of vasospasm is not feasible because the vessels are enclosed within the cranium and deep to the brain. Cerebral vasospasm may cause significant morbidity including stroke and death, and there is no reliable method to promptly detect it. Thus, a device, which can accurately determine distal vessel impedance using only proximal measurements is needed to safely and effectively evaluate certain vessel disease states. The terms proximal and distal are used in reference to the heart, with the heart being proximal and vessels away from the heart being distal.

BRIEF DESCRIPTION OF THE DRAWINGS

For a more complete understanding of the disclosed methods and apparatuses, reference should be made to the embodiments illustrated in greater detail in the accompanying drawings, wherein.

It should be understood that the drawings are not necessarily to scale and that the disclosed embodiments are sometimes illustrated diagrammatically and in partial views. In certain instances, details which are not necessary for an understanding of the disclosed methods and apparatuses or which render other details difficult to perceive may have been omitted. It should be understood, of course, that this disclosure is not limited to the particular embodiments illustrated herein.

DETAILED DESCRIPTION

The present disclosure is directed to vascular impedance measuring devices and methods of using the same. While the apparatuses and methods of the present disclosure may be embodied in many different forms, several specific embodiments are discussed herein with the understanding that the present disclosure is to be considered only as an exemplification of the principles of the disclosure, and it is not intended to limit the disclosure to the embodiments illustrated.

Figure 1:
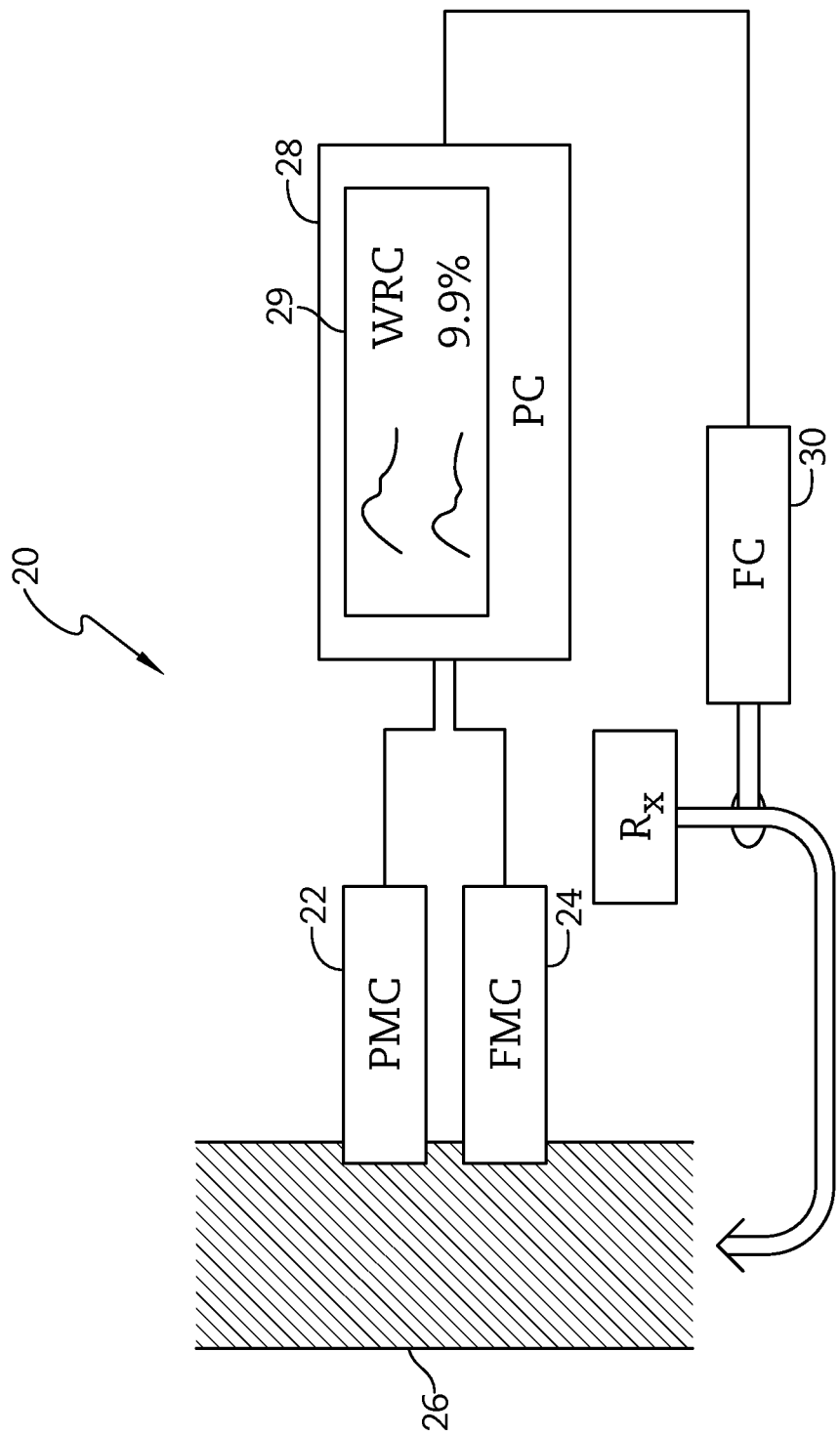
FIG. 1 depicts a diagram of general components of a first embodiment of a vascular impedance measuring device including pressure and flow measuring components.

A first embodiment of a vascular impedance measuring device 20 is depicted in FIG. 1. A pressure measuring component 22 and a flow measuring component 24 are attached to a target vessel or artery 26. Each of the pressure measuring component 22 and the flow measuring component 24 is operatively connected to a processing component 28. The processing component 28 may be any suitable processor that is capable of receiving data from the pressure measuring component 22 and the flow measuring component 24 and which is programmed to process the data, as will be described in greater detail hereinbelow. The processing component 28 may include a display 29, for example, a computer screen, a mobile device, or any other suitable display that is disposed within a housing or remote from the processing component and which may depict the processed data. In some embodiments, a feedback component 30 may also be operatively connected to the processor 28 to provide appropriate feedback in the form of therapy to the body. More specifically, the feedback component 30 receives data and/or directions from the processing component 28 and, based on the received data and/or directions, provides an effective means for a physician or operator to provide automated treatment to a patient or targeted artery based on, for example, an impedance calculated by the processing component 28 (or based on any other calculations provided by the processing component 28).

The vascular impedance measuring device 20, through the use of both a pressure measuring component 22 and the flow measuring component 24, can evaluate a distal impedance of a single artery. The present disclosure provides an effective means for a physician or operator to determine impedance of the distal vasculature, where the heart is proximal, of a single point in the arterial system.

The pressure measuring component 22 may record multiple waves of pressure related to heart cycles or pulse. The pressure measuring component 22 may record a discrete number of cycles, discrete duration of cycles, and/or record pressure waves continuously. The pressure wave data collected by the pressure measuring component 22 may be automatically transferred to the processing component 28, for example, in real-time or at any suitable interval of time. In alternative illustrative embodiments, the pressure wave data may be uploaded in any suitable manner to the processing component 28.

Figure 2:
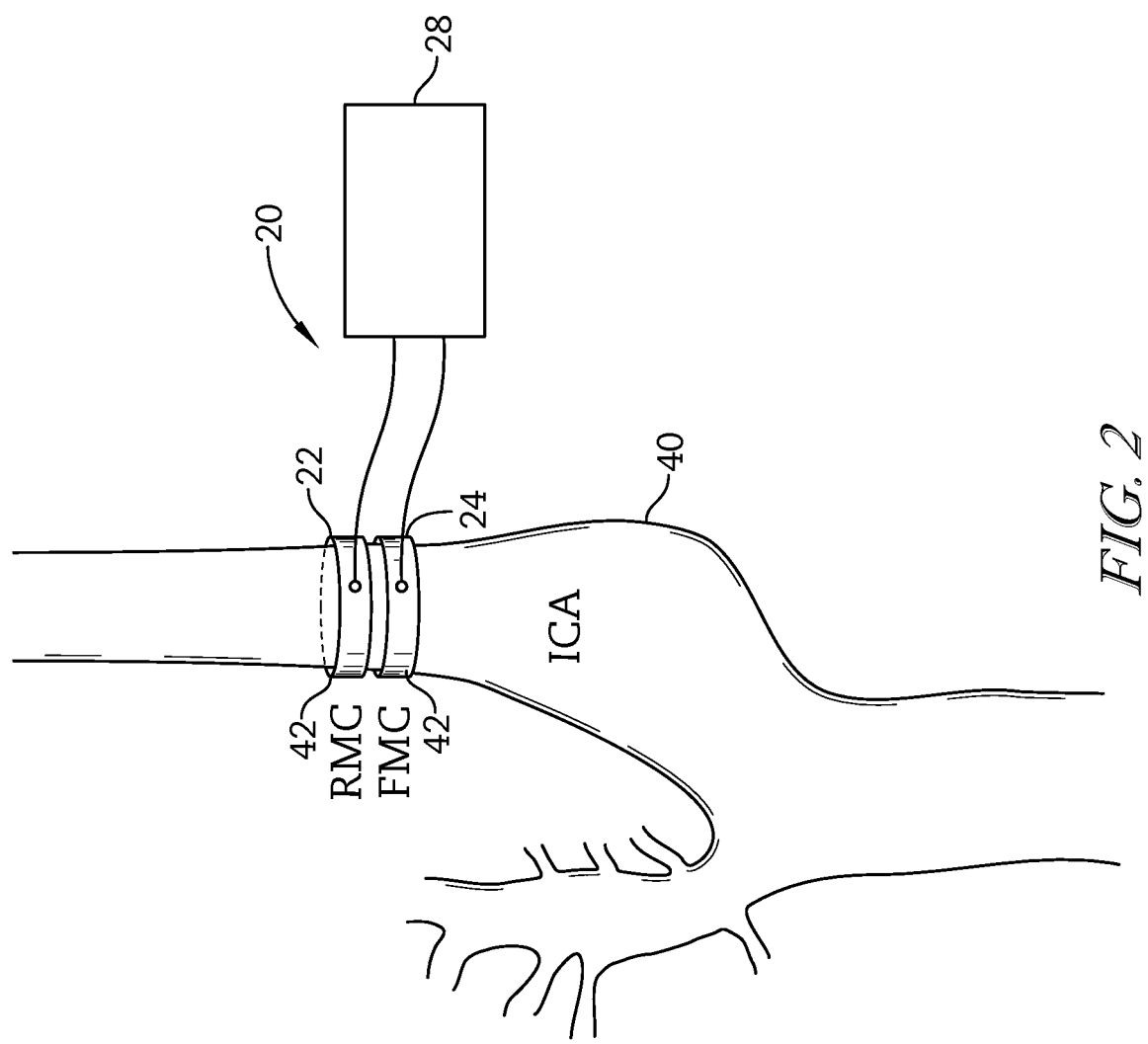
FIG. 2 depicts a second embodiment of a vascular impedance measuring device similar to the embodiment of FIG. 1 and including pressure and flow measuring components having cuffs disposed around the internal carotid artery of a patient, wherein the pressure measuring component in the form of a small Doppler ultrasound and the pressure measuring component is in the form of a tonometer.

In illustrative embodiments, the pressure measuring component 22 may be non-invasive using any number of methods, for example, applanation tonometry. In other illustrative embodiments, the pressure measuring component 22 may be implanted adjacent to a targeted vessel, for example, adjacent or around the internal carotid artery 40 with, for example, cuffs 42, as depicted in FIG. 2, using any number of methods including applanation tonometry or ultrasound. In still other illustrative embodiments, the pressure measuring component 22 may be implanted into the targeted vessel using any number of methods, including catheter-based pressure monitoring, electrical pressure monitoring with a wire probe, and/or any other suitable method. While FIG. 2 depicts the flow measuring component 24 and the pressure measuring component 22 as being adjacent the internal carotid artery 40, the embodiments of the present disclosure are not limited to such artery. In fact, the principles of the present disclosure or variations thereof may be applied to any suitable vessel or artery.

The flow measuring component 24 may record multiple waves of flow related to heart cycles or pulse. The flow measuring component 24 may record a discrete number of cycles, discrete duration of cycles, and/or record flow waves continuously. The flow wave data collected by the flow measuring component 24 may be automatically transferred to the processing component 28, for example, in real-time or at any suitable interval of time. In alternative illustrative embodiments, the flow wave data may be uploaded in any suitable manner to the processing component 28.

Figure 8:
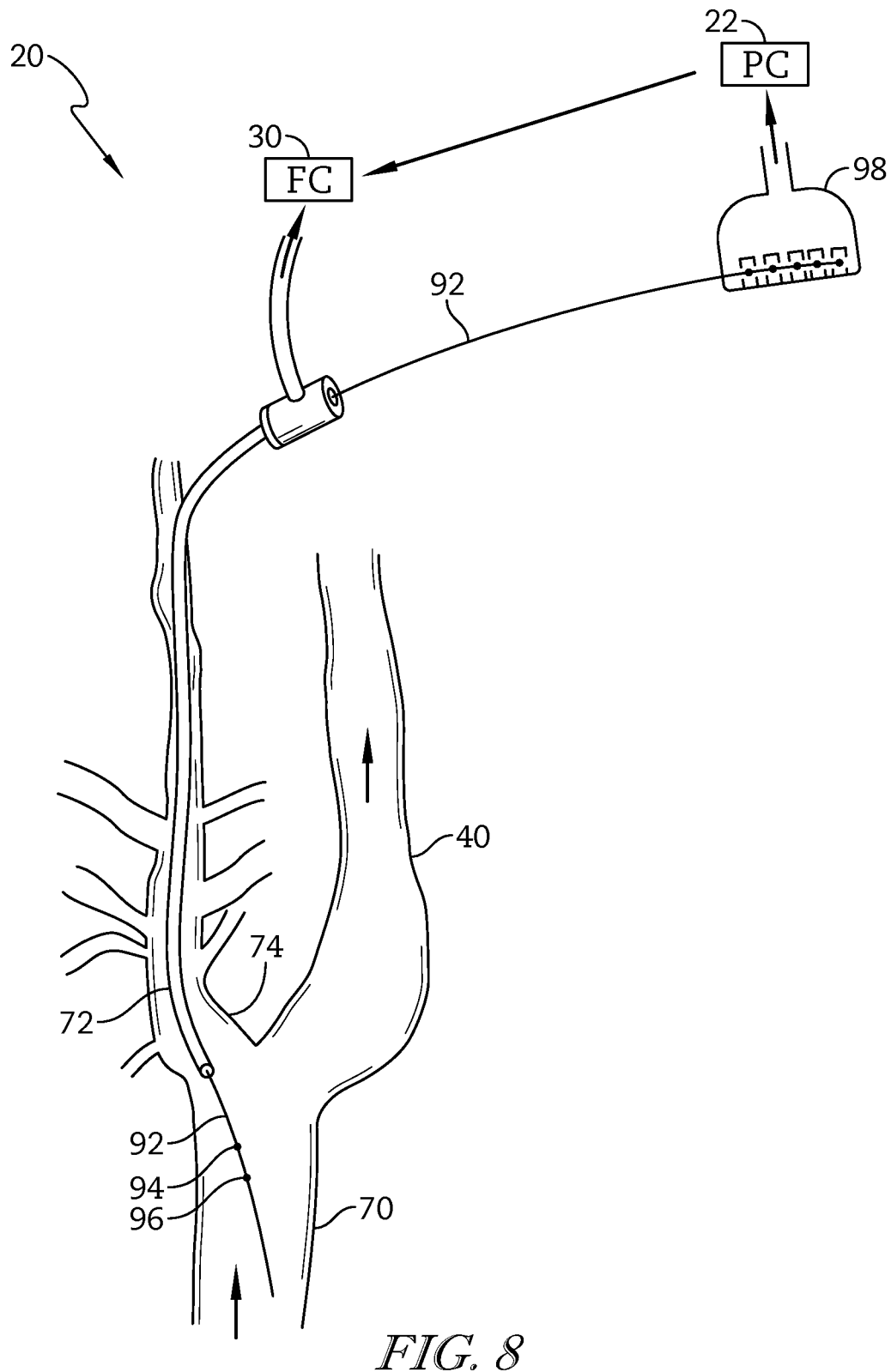
FIG. 8 depicts another embodiment of a vascular impedance measuring device using an intravascular wire capable of transducing both pressure and flow, a processing component, and feedback component.

In illustrative embodiments, the flow measuring component 24 may be non-invasive using any number of methods, for example, Doppler ultrasound. In other illustrative embodiments, the flow measuring component 24 may be implanted adjacent to a targeted vessel, for example, adjacent or around the internal carotid artery 40, as depicted in FIG. 2, using any number of methods including Doppler ultrasound. In still other illustrative embodiments, the flow measuring component 24 may be implanted into the targeted vessel using any number of methods, including a direct flow meter, ultrasound, and/or any other suitable method. In another embodiment, as shown in FIG. 8, the flow measuring component may be contained within a flow-wire 96.

Figure 3:
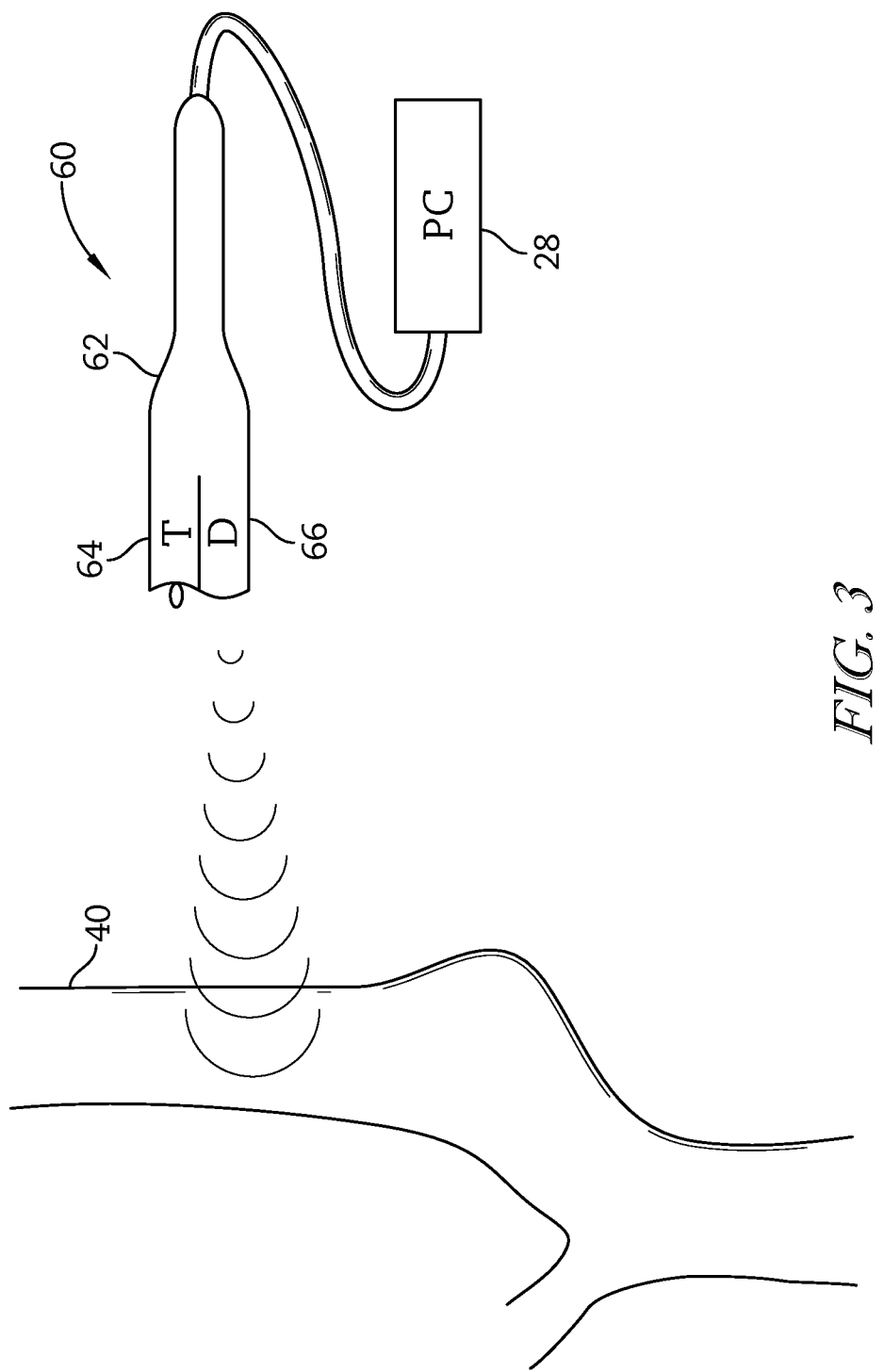
FIG. 3 depicts a third embodiment of a vascular impedance measuring device including a pressure measuring component and a flow measuring component combined into one non-invasive probe pressed against the internal carotid artery.

In a further illustrative embodiment, as depicted in FIG. 3, a vascular impedance measuring device 60 includes a pressure measuring component and a flow measuring component combined into one non-invasive probe 62 pressed against the internal carotid artery 40. A pressure signal may be obtained through applanation tonometry 64 through a first portion of the probe 62 and, simultaneously, flow data is obtained through an aligned Doppler ultrasound 66 in a second portion of the probe 62. The probe 62 transmits data to the processing component 28. A similar mechanism of data collection could be performed in other vessels.

Figure 4:
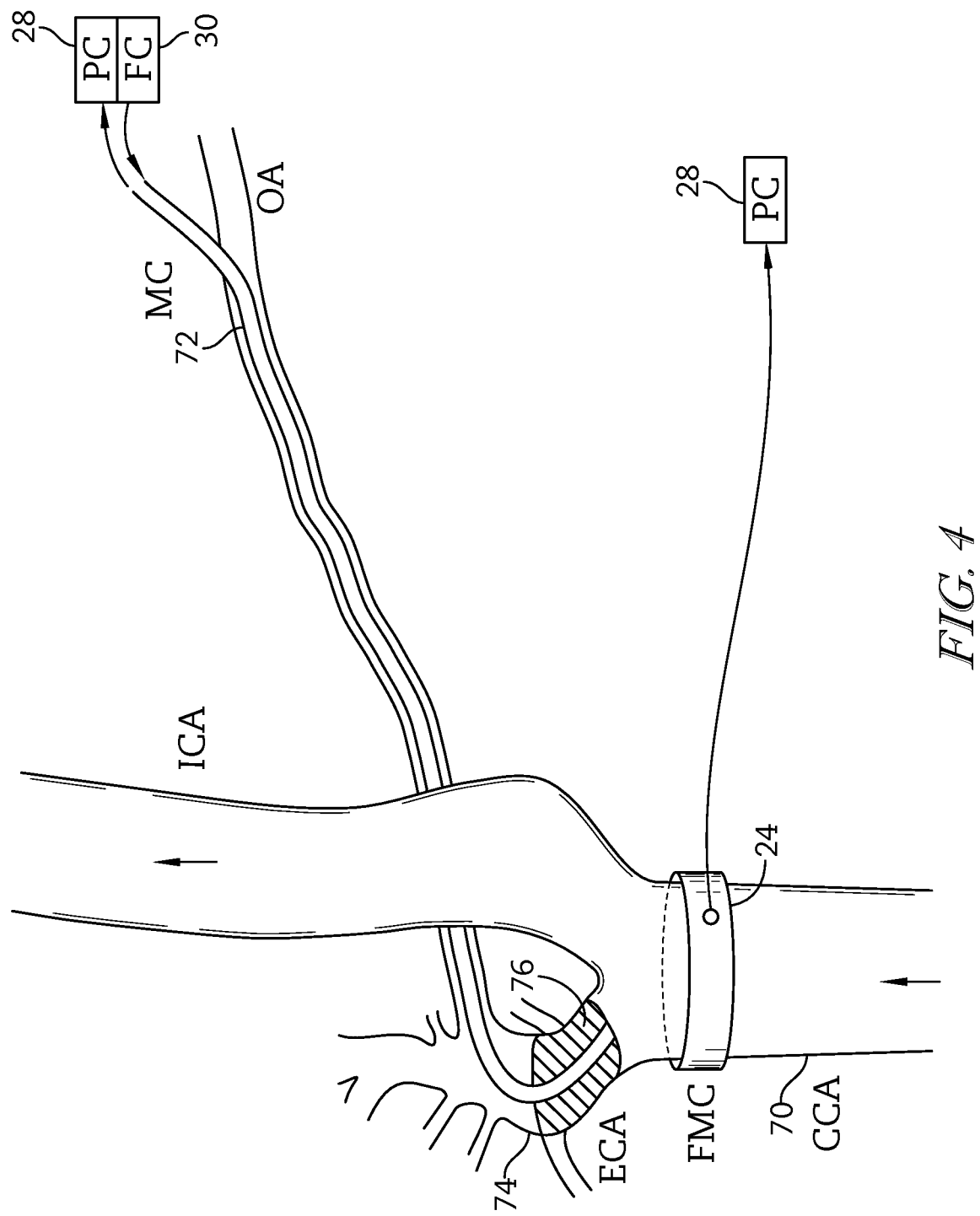
FIG. 4 depicts an embodiment of a vascular impedance measuring device used for internal carotid artery measurements in cerebral vasospasm and including a flow measuring component, a pressure measuring component, a processing component, and a feedback component for intra-arterial medication delivery.

In yet another illustrative embodiment, as depicted in FIG. 4, the flow measuring device 24 is depicted as being wrapped around the common carotid artery 70, but may alternatively be placed around the internal carotid artery or any other suitable artery or vessel. A microcatheter 72 may be introduced percutaneously into the occipital artery or other artery and positioned at the origin of the external carotid artery 74 or other artery adjacent to the site of flow measuring device placement. The microcatheter 72 allows pressure transduction and serves as the pressure measuring device. A balloon 76 may be mounted on a tip of the microcatheter 72, which allows isolation of the common and internal carotid arteries for both pressure measurement and delivery of therapeutics from the feedback component 30. Pressure from the microcatheter 72 and flow data from the flow measuring device 24 may be transmitted to the processing component 28, shown as two separate parts here. A similar mechanism of data collection and therapy delivery could be performed in other vessels.

Figure 5:
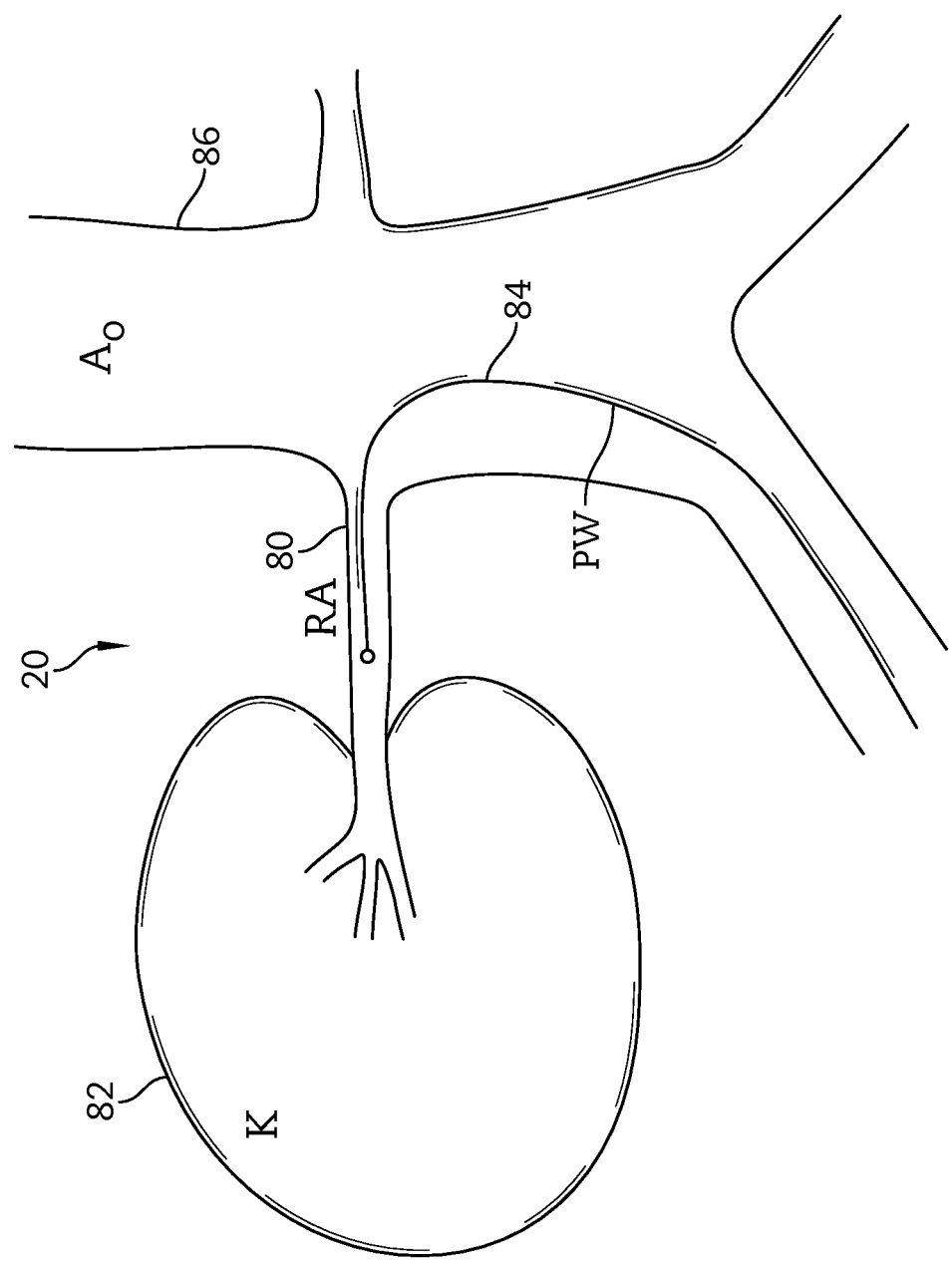
FIG. 5 depicts another embodiment of a vascular impedance measuring device used to assess the renal artery, which supplies blood to the kidney.

Another embodiment of the vascular impedance measuring device 20 is depicted in FIG. 5. The device 20 is depicted as being used to assess the renal artery 80, which supplies blood to the kidney 82. Such an implementation would be useful for intermittent assessment of renal artery stenosis or fibromuscular dysplasia to determine progression of disease. A pressure-measuring wire 84 may be introduced into the renal artery 80 through the aorta 86. Flow data may be obtained from the flow measuring component 24 in the form of a non-invasive Doppler ultrasound, for example. A similar mechanism of data collection could be performed in other vessels.

Another embodiment of the vascular impedance measuring device 20 is depicted in FIG. 8. The device uses a wire 92, which has a pressure-measuring component 94 and a flow-measuring component 96 built into it. [Such a wire is currently commercially available]. The wire can be inserted through a percutaneously inserted microcatheter 72. The pressure 94 and flow 96 measuring components are connected through the wire 92 to a connector 98, which transfers the signals to the processing component 22. The processing component may deliver signals to a feedback component 30, which is capable of therapeutic intervention.

The processing component 28 may perform any suitable functions, for example, characterization of data received from the flow measuring component 22, characterization of data from the pressure measuring component 24, synchronization of flow and pressure data, derivation of reservoir, or steady state, or non-wave-related pressure, derivation of forward and backward waves, display of waves and wave components, display of a vascular impedance value, display of a wave reflection coefficient, signal transmission to the feedback component 30 for delivery of therapy, and/or any other suitable functions. While a number of different functions are disclosed, one skilled in the art will understand that the processing component 28 may implement any one or more of the functions disclosed herein.

Figure 6:
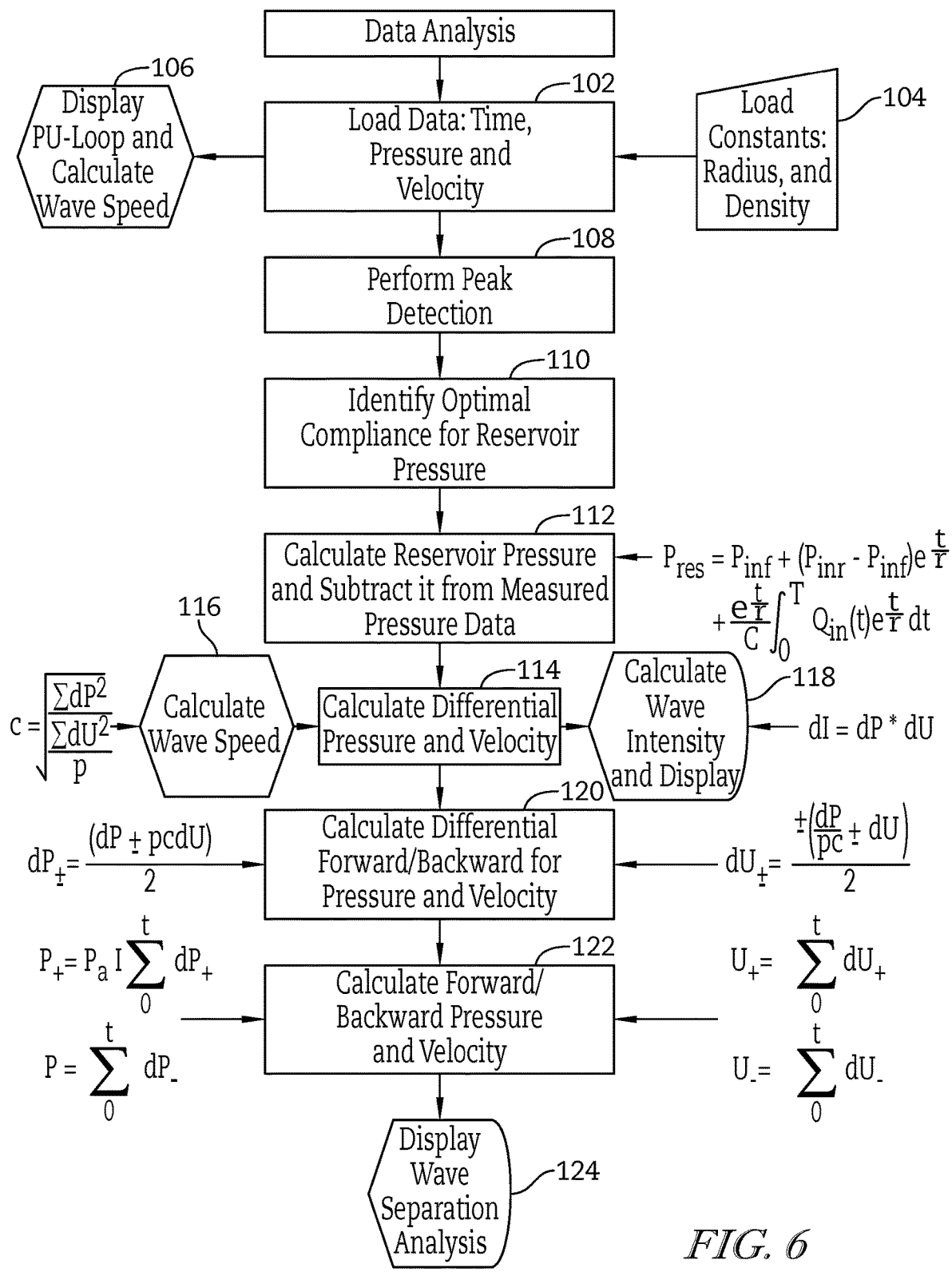
FIG. 6 depicts a flow-chart diagram of the processing steps undertaken by one embodiment of the processing component.

A flow diagram depicting a data analysis that may be performed using the flow and/or pressure data is depicted in FIG. 6. The data analysis begins at block 100 of FIG. 6 and moves to block 102, wherein data, such as time, pressure, and velocity are loaded based on constants, such as radius and density, received from block 104. The PU-loop (pressure v. speed) may be displayed and speed of the wave may be calculated at block 106. Peak detection is thereafter performed at block 108, wherein the highest amplitude point of both flow and pressure waves can be detected and synchronized.

In illustrative embodiments, the processing component 28 may characterize raw data from the flow measuring component 22 by separating the flow component data into waves. This may be accomplished through peak detection or any other suitable method. For elimination of noise within the raw data, the flow component data may be averaged over a length of time or number of cycles to produce an averaged flow wave.

In illustrative embodiments, the processing component 28 may characterize raw data from the pressure measuring component 24 by separating the pressure component data into waves. This may be accomplished through peak detection or any other suitable method. For elimination of noise within the raw data, the pressure component data may be averaged over a length of time or number of cycles to produce an averaged pressure wave.

In illustrative embodiments, the processing component may synchronize the data from the pressure and flow measurement components. The synchronization may be accomplished with peak detection or any other suitable method.

After peak detection is performed at block 108, processing is passed to block 110, wherein an optimal compliance for reservoir pressure is selected. Thereafter, at block 112, the processing component 28 may derive the reservoir pressure of the system (i.e., patient) at block 114, which represents the blood pressure of the system independent of propagating waves. The reservoir pressure of the system may be calculated using the windkessel model on pressure and velocity data collected. First, an exponential decay fit may be applied to the diastolic portion of a collection pressure wave past its maximum value. The decay fit may be further improved using initially determined values and the collected velocity data. Finally, the arterial compliance may be determined and the reservoir pressure calculated. The reservoir pressure may be subtracted from measured pressure data. The differential pressure and velocity are then calculated at block 114 based on a calculation of wave speed from block 116. The differential pressure and velocity are then used at block 118 to calculate and display a wave intensity.

The processing component 28 may thereafter calculate differential forward/backward for pressure and velocity at block 120 and calculate forward/backward pressure and velocity at block 122. The wave separation analysis may be displayed at block 124.

The processing component 28 may derive the forward and backward waveforms. After subtracting reservoir pressure from a total pressure, a pressure waveform may be derived. The pressure waveform may be expressed in the time domain or the frequency domain. Given the pressure and flow waveforms, forward and backward waves may be derived using a set of differential equations. This is possible because the forward flow and pressure waves have positive amplitude, but the backward pressure wave has positive amplitude, while the backward flow wave has negative amplitude. The waveforms and waveform components may be displayed by the processing component 28.

After deriving the forward and backward waves, the processing component 28 may calculate impedance directly using Ohm's law (impedance=pressure/flow). The value of vascular impedance distal to the site of measurement may be displayed by the processing unit 28 on a display, as noted above.

The processing component 28 may derive the wave intensity of the forward and backward waves, where wave intensity equals pressure multiplied by flow. Using this wave intensity calculation, the processing unit 28 may display a wave reflection coefficient, equal to backward wave divided by forward wave, that rises as distal impedance rises.

The processing component 28 may send a signal based on one or more parameters to the feedback component 30. The parameters may be impedance, wave reflection coefficient, and/or any other calculated value.

The feedback component 30 may allow therapeutic intervention. In illustrative embodiments, the feedback component 30 may suggest a therapeutic intervention to the physician or operator. In other illustrative embodiments, the feedback component 30 may deliver an intravenous medication. In still further illustrative embodiments, the feedback component 30 may deliver intra-arterial medication to the vessel 26 being monitored. In further illustrative embodiments, the feedback component 30 may alert the patient to alter behavior or seek medical attention. Other embodiments of feedback may be employed and/or the feedback component 30 may provide any combination of the foregoing methods of feedback.

In an illustrative embodiment of the feedback component 30, an intra-arterial catheter may be placed in or adjacent to the target vessel 26. The intra-arterial catheter may be used as part of the pressure measuring component 22 and the feedback component 30 to deliver intra-arterial medication.

In illustrative embodiments of the vascular impedance measuring device, the device may be used to monitor and/or treat cerebral vasospasm following subarachnoid hemorrhage. In such embodiments, the pressure and flow measuring components may be implanted to allow continuous monitoring. In this embodiment the processing and feedback components may provide continuous, optimized therapy. This therapy may include delivery of cardiac and vasoactive medications to optimize blood pressure and heart rate. It may include delivery of intra-arterial spasmolytic agents to treat vasospasm.

Figure 7A:
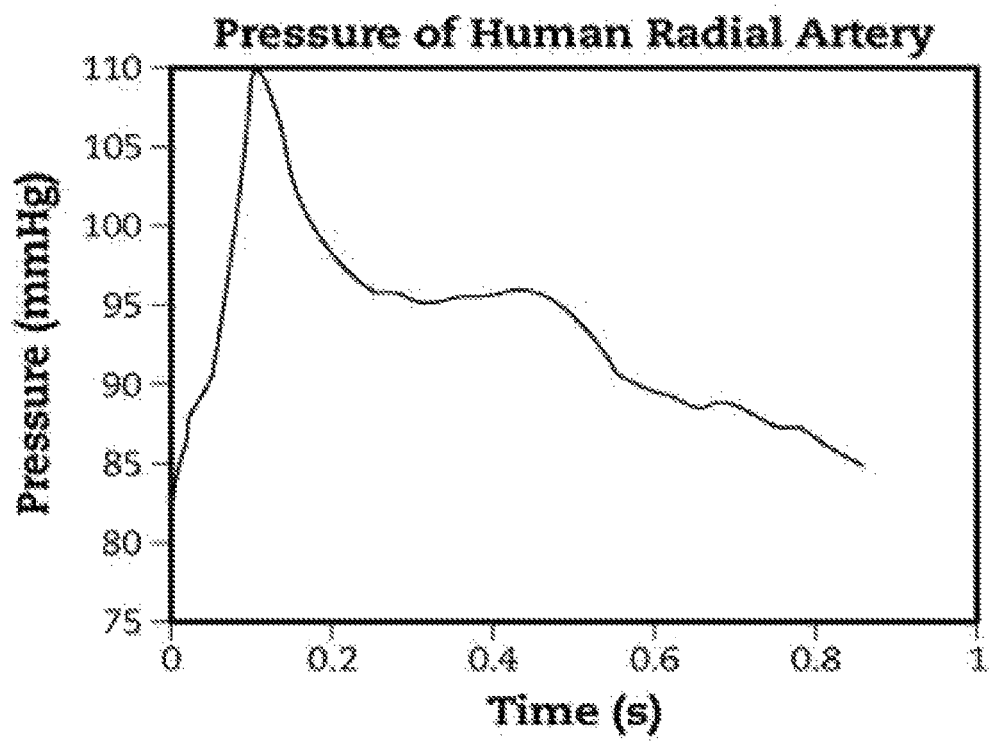
FIGS. 7A-7F depict waveform analyses derived from evaluation of a human radial artery using a prototype of the vascular impedance measuring device FIG. 1.
Figure 7B:
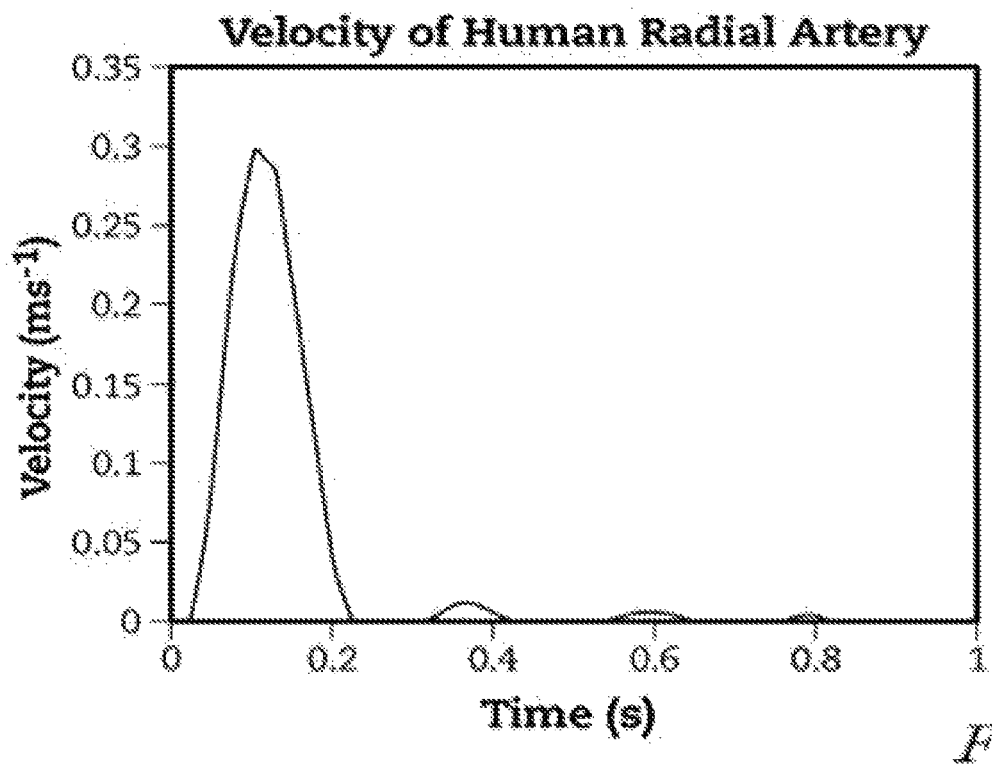
Figure 7C:
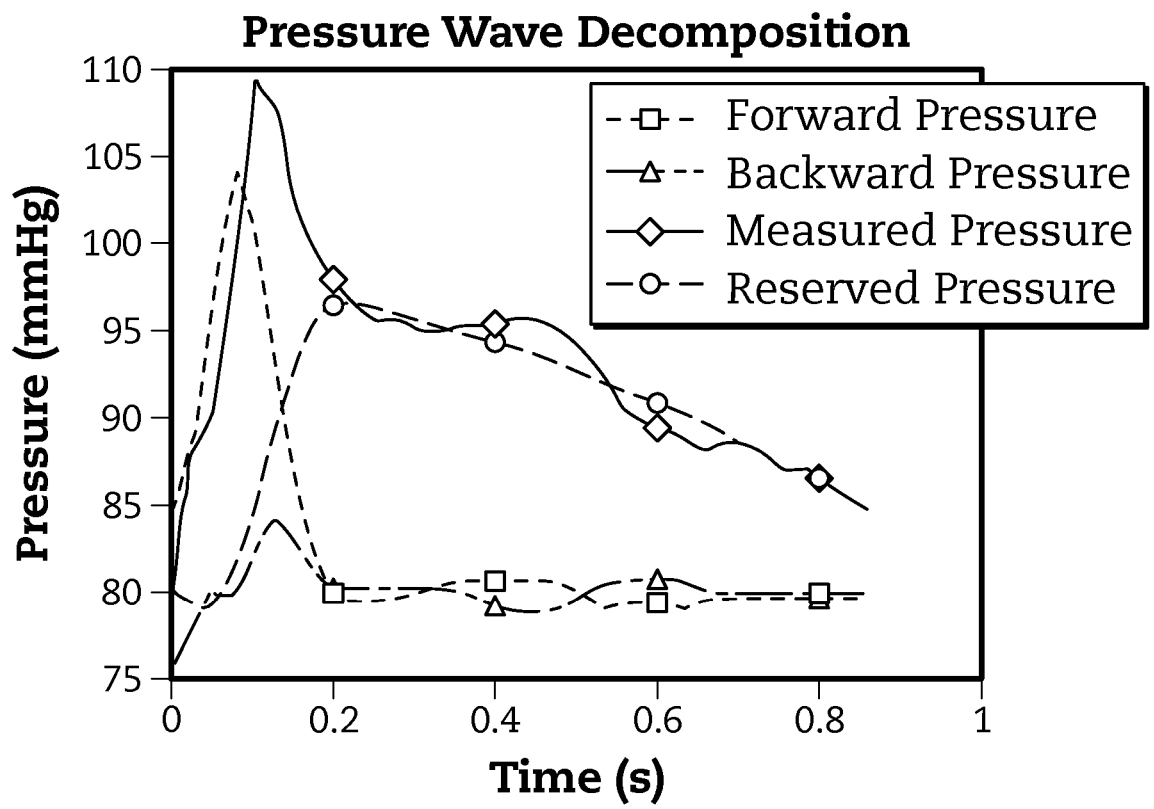
Figure 7D:
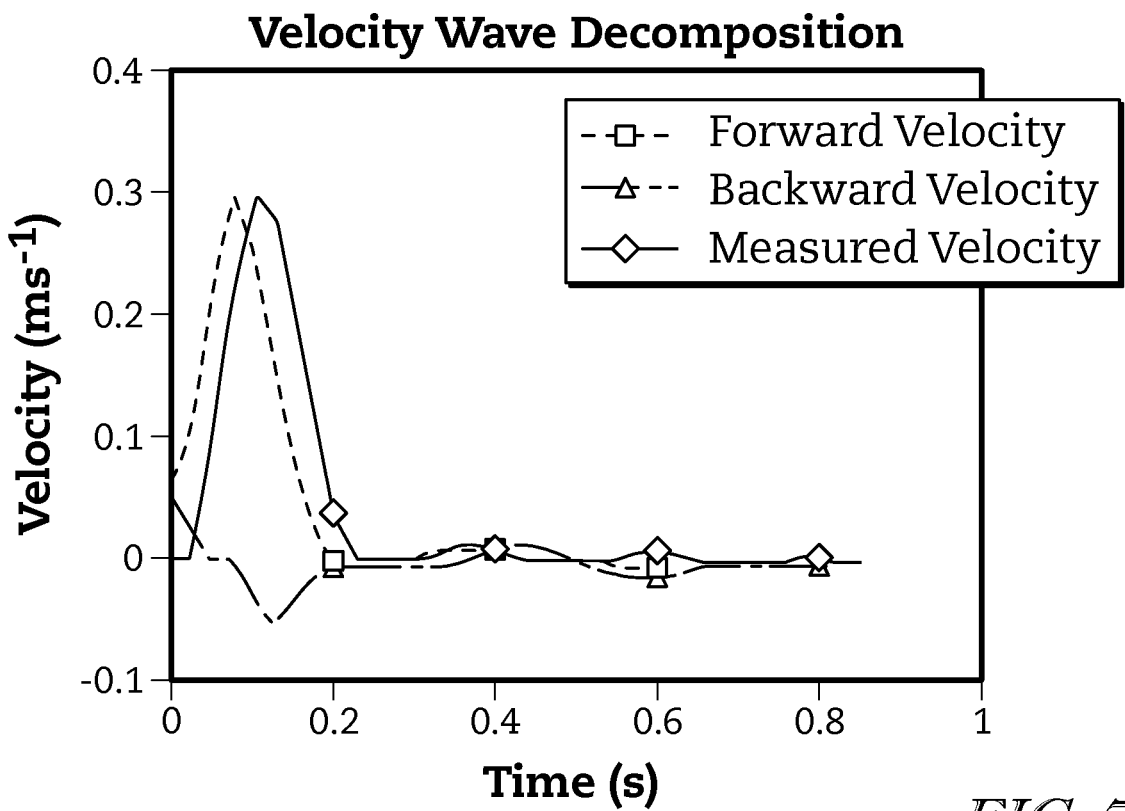
Figure 7E:
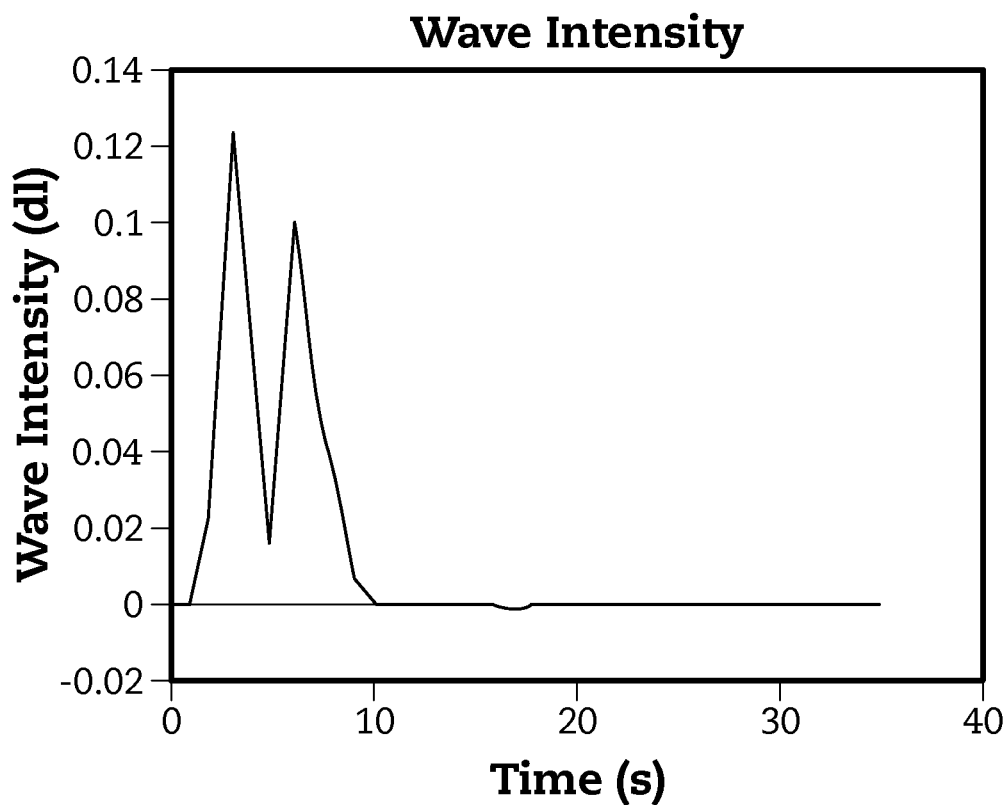
Figure 7F:
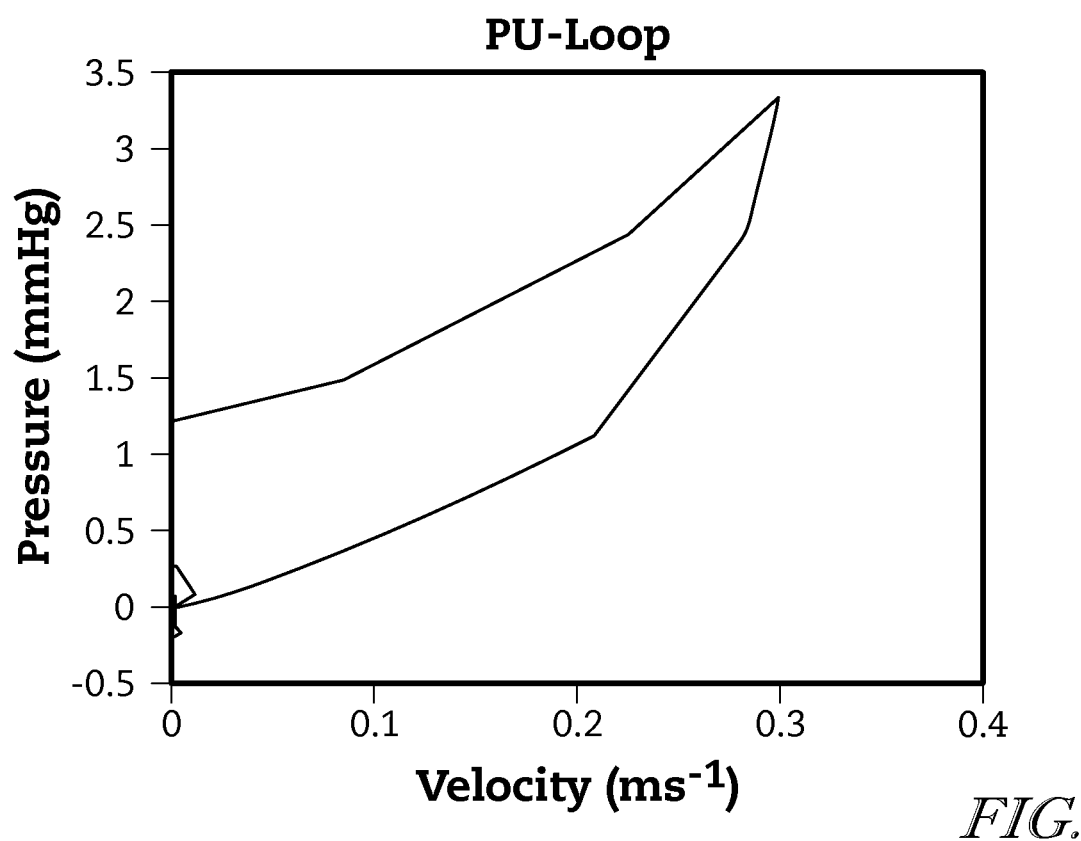

FIGS. 7A-7F show pressure and velocity waveforms following recording and analysis. More particularly, FIGS. 7A and 7B depict a pressure within a human radial artery as a function of time and a velocity of the human radial artery as a function of time, respectively. FIG. 7C depicts pressure waveform separation as measured pressure (blue), forward pressure (red), backward pressure (green), and reservoir pressure (black). The forward and backward pressure is shifted up by minimum diastolic pressure to fit into the axes. The wave separation is performed on one cardiac cycle and its corresponding velocity. FIG. 7D depicts velocity waveform separation as the measure velocity (blue), forward velocity (red), and backward velocity (green). The wave separation is performed on one cardiac cycle and its corresponding velocity. FIG. 7E depicts wave intensity over time and FIG. 7F depicts the PU-loop, which shows pressure as a function of velocity.

INDUSTRIAL APPLICABILITY

Assessment and treatment of cerebral vasospasm following aneurysmal subarachnoid hemorrhage remain somewhat ineffective in preventing delayed cerebral ischemia. Hourly clinical assessment is highly subjective. Daily transcranial Doppler assessment is unreliable and subject to many variables affecting blood velocity other than cerebral vasospasm. The pressure measuring component of the present disclosure and the dual waveform analysis presented herein control for confounding variables to provide a reliable assessment of intracranial vascular resistance. The devices presented herein may fill a large gap in care, with the potential to prevent devastating post-hemorrhage strokes.

Continuous vasospasm monitoring with the devices presented herein may allow patients to be treated in intensive care units for a shorter duration of time. The period of risk for cerebral vasospasm is 2-3 weeks following aneurysmal subarachnoid hemorrhage. Most patients require at least one week of intensive care for vasospasm monitoring even if they do not have other intensive care needs. The devices presented may allow early transfer of patients to general monitoring units or rehabilitation units, thus saving enormous health care expenses of intensive care.

The devices presented herein may serve as research tools to give high-quality feedback for investigational cerebral vasospasm treatment. Currently employed interventions, even when promptly and appropriately applied, provide only modest benefit. It is difficult to study the effects of investigational treatment because, assessment of cerebral vasospasm is currently limited. The devices presented herein may play a significant role in future clinical trials for cerebral vasospasm interventions.

Existing devices can approximate resistance by measuring the pressure at two points in the arterial tree. This provides a resistance approximation for the vessel between those two points. Existing devices cannot determine the resistance or impedance distal to a single point. Thus, the devices presented herein may provide data for end-organ arterial stenosis, including but not limited to, those within the coronary arteries to the heart and the renal arteries to the kidneys.

Sometimes a vessel will have multiple sites of stenosis, and it will be unclear which site is causing symptoms. One such condition is tandem stenosis of the cervical internal carotid artery and intracranial carotid artery. In this situation, it is important to treat the diseased vessel, but it may be hazardous to treat both sites of stenosis if only one is preventing adequate flow to the brain. The devices presented herein may allow a physician or operator to determine the segmental impedance at each site to guide treatment.

While only certain embodiments have been set forth, alternatives and modifications may be apparent from the above description to those skilled in the art. These and other alternatives are considered equivalents and within the spirit and scope of this disclosure and the appended claims. Any of the embodiments disclosed herein may also be used on any artery or vessel and in any manner.

I claim:

1. A vascular impedance measuring device for a vessel having a radius comprising:
   a processing component capable of processing raw pressure and flow wave data;
   a pressure measuring component capable of providing pressure wave data from a specified point in the vessel and forwarding the pressure wave data to the processing component;
   a flow measuring component capable of providing flow wave data from the specified point or a point near the specified point in the vessel and forwarding the flow wave data to the processing component;
   wherein the processing component processes the raw pressure and flow wave data to produce an estimation of vascular impedance of the vessel from the specified point of measure, the processing component treating the radius of the vessel as a constant, and
   wherein a feedback component is in communication with the processing component and is capable of delivering or titrating a therapeutic intervention based on derived impedance parameters of the processing component.

2. The vascular impedance measuring device of claim 1, wherein the pressure measuring component is noninvasive to a body in which the vessel is disposed.

3. The vascular impedance measuring device of claim 1, wherein the pressure measuring component is applied to the vessel and is invasive to a body in which the vessel is disposed.

4. The vascular impedance measuring device of claim 1, wherein the pressure measuring component is intravascular.

5. The vascular impedance measuring device of claim 1, wherein the flow measuring component is noninvasive to a body in which the vessel is disposed.

6. The vascular impedance measuring device of claim 1, wherein the flow measuring component is applied to the vessel and is invasive to a body in which the vessel is disposed.

7. The vascular impedance measuring device of claim 1, wherein the flow measuring component is intravascular.

8. The vascular impedance measuring device of claim 1, wherein the processing component provides a single or discrete assessment of vascular impedance.

9. The vascular impedance measuring device of claim 1, wherein the processing component provides a continuous assessment of vascular impedance.

10. The vascular impedance measuring device of claim 1, wherein the processing component derives a value for vascular impedance, which may be presented in amplitude or phase.

11. The vascular impedance measuring device of claim 1, wherein the processing component derives values for reservoir pressure, total wave intensity, forward wave intensity, backward wave intensity, and wave reflection percentage.

12. The vascular impedance measuring device of claim 1, wherein the processing component derives and may graphically or numerically display the values of one or more of:
   averaged pressure waveform, amplitude, and period;
   averaged flow waveform, amplitude, and period;
   reservoir pressure, which is the blood pressure of the system independent of propagating waves;
   forward pressure waveform and/or amplitude;
   backward pressure waveform and/or amplitude;
   forward flow waveform and/or amplitude;
   backward flow waveform and/or amplitude;
   forward wave intensity;
   backward wave intensity;
   vascular impedance, which may presented in amplitude and phase, or other form; and
   a target heart rate or rates, which would optimize the resistance component of impedance to allow maximum blood flow through the measured arterial system.

13. The vascular impedance measuring device of claim 1, wherein the feedback component alerts the physician, operator, or patient to critical parameter values.

14. The vascular impedance measuring device of claim 1, wherein the feedback component titrates an amount of intravenous therapy based on the parameters derived by the processing unit.

15. The vascular impedance measuring device of claim 1, wherein the feedback component titrates an amount of intra-arterial therapy delivered to a specified vascular territory based on the parameters derived by the processing unit.

16. The vascular impedance measuring device of claim 1, wherein the device is entirely implanted within the body, output is transmitted wirelessly, and the feedback component functions are controlled wirelessly.

17. The vascular impedance measuring device of claim 1, wherein a common intravascular catheter is used for the pressure measuring component and part of the feedback component for medication delivery.

* * * * *